US007718261B2

(12) United States Patent
Katusic et al.

(10) Patent No.: US 7,718,261 B2
(45) Date of Patent: *May 18, 2010

(54) NANOSCALE ZINC OXIDE, PROCESS FOR ITS PRODUCTION AND USE

(75) Inventors: Stipan Katusic, Kelkheim (DE); Günther Michael, Karlstein (DE); Peter Kress, Freigericht (DE); Geoffrey J. Varga, Freigericht (DE); Edwin Staab, Geiselbach (DE); Winfried Weber, Hünfelden (DE)

(73) Assignee: Evonik Degussa GmbH, Essen (DE)

( * ) Notice: Subject to any disclaimer, the term of this patent is extended or adjusted under 35 U.S.C. 154(b) by 1667 days.

This patent is subject to a terminal disclaimer.

(21) Appl. No.: 10/505,415

(22) PCT Filed: Mar. 10, 2003

(86) PCT No.: PCT/EP03/02421

§ 371 (c)(1),
(2), (4) Date: Aug. 24, 2004

(87) PCT Pub. No.: WO03/080515

PCT Pub. Date: Oct. 2, 2003

(65) Prior Publication Data

US 2005/0069506 A1    Mar. 31, 2005

(30) Foreign Application Priority Data

Mar. 22, 2002   (DE)   ................. 102 12 680

(51) Int. Cl.
*B32B 5/16* (2006.01)
*A61K 9/14* (2006.01)

(52) U.S. Cl. ..................... 428/402; 424/489

(58) Field of Classification Search ............... 428/402; 424/489
See application file for complete search history.

(56) References Cited

U.S. PATENT DOCUMENTS

| 77,618 | A | * | 5/1868 | Hunter | ................. 75/658 |
| 2,013,980 | A | * | 9/1935 | Bunce | ................. 423/108 |
| 2,200,873 | A | * | 5/1940 | Cyr | ................. 423/107 |

(Continued)

FOREIGN PATENT DOCUMENTS

GB   435 005   9/1935

(Continued)

OTHER PUBLICATIONS

Wang et al., J. Applied Polymer Sicence, 1998, 68, pp. 1219-1225.*

(Continued)

*Primary Examiner*—Johann R Richter
*Assistant Examiner*—Abigail Fisher
(74) *Attorney, Agent, or Firm*—Oblon, Spivak, McClelland, Maier & Neustadt, L.L.P.

(57) ABSTRACT

Nanoscale, pyrogenically produced zinc oxide having a BET surface area of 10 to 200 m²/g, which is in the form of aggregates of anisotropic primary particles and whereby the aggregates display an average diameter of 50 to 300 nm. It is obtained from zinc powder, which is converted to zinc oxide powder in the four successive reaction zones, evaporation zone, nucleation zone, oxidation zone and quench zone. It can be used in sunscreen formulations.

25 Claims, 2 Drawing Sheets

U.S. PATENT DOCUMENTS

| | | | | |
|---|---|---|---|---|
| 4,448,608 A * | 5/1984 | Jenkins et al. | ............... | 106/428 |
| 5,441,726 A | 8/1995 | Mitchnick et al. | | |
| 5,560,871 A * | 10/1996 | Yoshimaru et al. | ...... | 252/519.53 |
| 5,876,688 A * | 3/1999 | Laundon | ..................... | 423/622 |
| 7,371,337 B2 * | 5/2008 | Katusic et al. | ............... | 252/500 |
| 2005/0182174 A1* | 8/2005 | Michael et al. | ............ | 524/430 |
| 2006/0073092 A1* | 4/2006 | Katusic et al. | ............... | 423/622 |
| 2007/0037699 A1 | 2/2007 | Katusic et al. | | |

FOREIGN PATENT DOCUMENTS

| | | |
|---|---|---|
| JP | 07 118133 | 5/1995 |
| JP | 11-278838 | 10/1999 |

OTHER PUBLICATIONS

Spencer, Topics in Catalysis, 1999, 8, 259-266.*

Funahashi, Tsuneo et al. "Manufacture of Zinc Oxide Fine Particles with Large Specific Surface Area", Chemical Abstracts & Indexes, vol. 109, No. 22, XP000019653 1988.

* cited by examiner

NANOSCALE ZINC OXIDE, PROCESS FOR ITS PRODUCTION AND USE

The invention provides nanoscale, pyrogenically produced zinc oxide powder, a process for its production and its use.

Many types of zinc oxide powders are described. These powders are used in paints, coatings, in resins and fibres. An important segment is the use of zinc oxide powders in the cosmetics area, particular as an ingredient in sunscreen formulations.

In principle there are two possibilities for synthesising zinc oxide powders, wet chemical processes and gas phase processes. In wet chemical processes, zinc compounds that can be converted to zinc oxide by a thermal reaction, such as zinc hydroxide, zinc oxalate or zinc carbonate, are generally used as the starting material. The disadvantage of the wet chemical method is that the zinc oxide particles that are produced agglomerate to larger units, which in cosmetic applications in particular are undesirable. The process, which is usually performed as a batch process, involves filtering and drying the particles, which is relatively cost-intensive.

Furthermore, impurities arising from the process and starting materials can only be removed from the finished product with great difficulty, if at all.

Gas phase processes or pyrogenic processes allow a more cost-effective process. These include the French and American processes that are used to produce zinc oxide on an industrial scale.

Both processes involve the oxidation of zinc vapour. The disadvantage here is the formation of large aggregates of primary particles and a small BET surface area.

The prior art describes various possibilities for gas phase synthesis with the aim of achieving a larger BET surface area, improved transparency and higher UV protection. Ultimately all of these experiments have the oxidation of zinc vapour in common.

JP 56-120518 describes the oxidation of zinc vapour with air or oxygen to form non-aggregated, acicular zinc oxide particles, which can often be incorporated into sunscreen formulations only with difficulty.

U.S. Pat. No. 6,335,002 describes the oxidation of zinc vapour with air or oxygen. By varying the process parameters, primary particles that are substantially isotropic in shape and have a low degree of aggregation are said to be formed, although no definition of the degree of aggregation is provided. The zinc vapour is oxidised in a flame of $H_2$ or propane and air or oxygen, whereby an excess of oxygen is used.

Overall, regardless of production, the prior art provides numerous types of zinc oxide in acicular, spherical, tetrahedral, rod and flake form, as described for example in U.S. Pat. No. 5,441,226.

The prior art illustrates the keen interest in zinc oxide, particularly in its use as UV protection in sunscreen formulations.

The object of the present invention is to provide a zinc oxide powder that displays high transparency combined with good UV protection. It should further be able to be readily incorporated into dispersions. Furthermore the object is to provide a process for the production of zinc oxide powder.

The object is achieved by a nanoscale, pyrogenically produced zinc oxide powder having a BET surface area of 10 to 200 $m^2/g$, characterised in that it is in the form of aggregates of anisotropic primary particles and that the aggregates display an average diameter of 50 to 300 nm.

A more complete appreciation of the invention and many of the attendant advantages thereof will be readily obtained as the same becomes better understood by reference to the following detailed description when considered in connection with the accompanying drawings, wherein.

Figure 1:
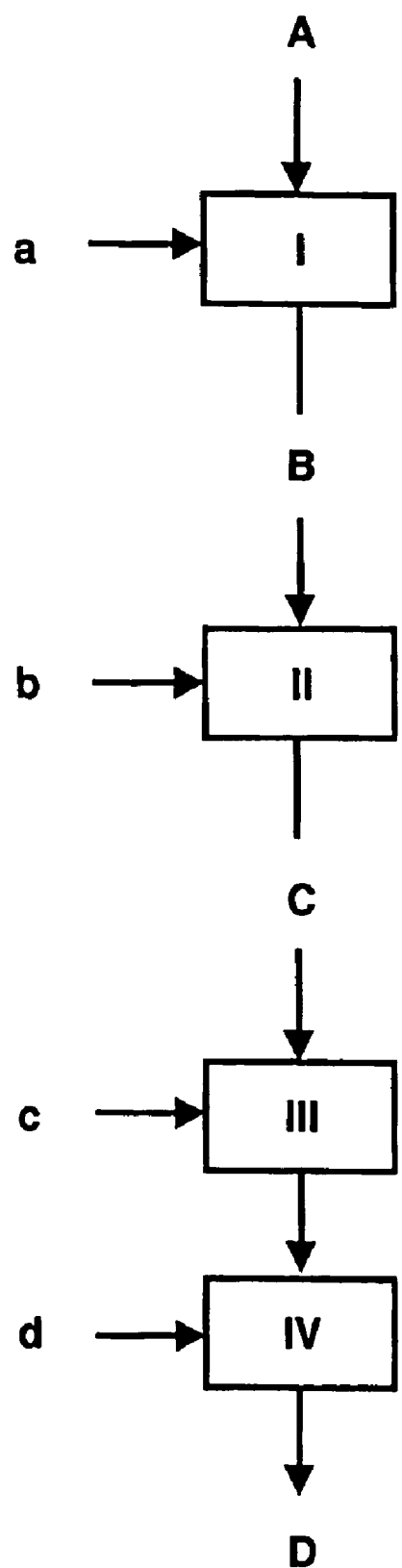
FIG. 1 shows a flow diagram of a process according to the invention with the process stages and the incoming and outgoing mass flows.

The primary particles are understood to be the smallest particles in high-resolution TEM images, which are obviously unable to be broken down any further. Several primary particles can congregate at their points of contact to form aggregates. These aggregates are either impossible or very difficult to break down again using dispersing devices. Several aggregates can join together loosely to form agglomerates, whereby this process can be reversed again by suitable dispersion.

The term anisotropic means that the arrangement of atoms differs along the three spatial axes. Anisotropic primary particles include for example those that are acicular, nodular or platelet-shaped. A cubic or spherical arrangement, for example, would be isotropic.

Pyrogenic refers to the formation of oxides by flame oxidation of metals or non-metals or compounds thereof in the gas phase in a flame produced by reaction of a fuel gas, preferably hydrogen, and oxygen. Highly disperse, non-porous primary particles are initially formed which, as the reaction continues, coalesce to form aggregates, and these can congregate further to form agglomerates.

In a particular embodiment the aggregates can comprise a mixture of nodular primary particles and acicular primary particles, whereby the ratio of nodular to acicular primary particles can be between 99:1 and 1:99.

The nodular primary particles preferably display an average diameter of 10 to 50 nm and the acicular primary particles preferably display a length of 100 nm to 2000 nm and a width of 10 nm to 100 nm.

The aggregates in the powder according to the invention can display a largely anisotropic structure, defined by a shape factor F(circle) of below 0.5. The variable F(circle) describes the deviation of an aggregate from a perfect circular shape. In a perfect circular object F(circle) equals 1. The lower the value, the further removed the object structure from the perfect circular shape. The parameter is defined according to ASTM 3849-89.

The powder according to the invention can display at its surface an oxygen concentration as non-desorbable moisture in the form of Zn—OH and/or Zn—$OH_2$ units of at least 40%. It is determined by XPS analysis (XPS=X-ray photoelectron spectroscopy) of the oxygen signals at 532 to 533 eV and 534 to 535 eV.

The powder according to the invention can preferably display a transmission of no more than 60% at a wavelength of 310 nm and 360 nm.

In a particular embodiment the bulk density of the powder according to the invention is 40 to 120 g/l.

The invention also provides a process for the production of the powder according to the invention, which is characterised in that zinc powder is converted into zinc oxide powder in four successive reaction zones, evaporation zone, nucleation zone, oxidation zone and quench zone, whereby in the evaporation zone the zinc powder conveyed there by an inert gas stream is evaporated in a flame of air and/or oxygen and a fuel gas, preferably hydrogen, under the proviso that the reaction parameters are chosen such that oxidation of the zinc does not occur, and whereby in the nucleation zone, where the hot reaction mixture, consisting of zinc vapour, water vapour as a reaction product of the flame reaction and optionally excess fuel gas, arrives from the evaporation zone, it cools to temperatures below the boiling point of zinc or is cooled by means of an inert gas, and whereby in the oxidation zone the mixture from the nucleation zone is oxidised with air and/or oxygen, and whereby in the quench zone the oxidation mixture is cooled to temperatures of below 400° C. by addition of cooling gas (for example nitrogen, air, argon, carbon dioxide).

The process can be performed in such a way that in the evaporation zone an excess of fuel gas is used, expressed in lambda values of 0.5 to 0.99, preferably 0.8 to 0.95.

In a particular embodiment the process can be performed in such a way that the temperature in the evaporation zone is preferably between 920° C. and 2000° C. In the nucleation zone the temperature can preferably be between 500° C. and 900° C., particularly preferably between 700° C. and 800° C.

Furthermore the cooling rate in the nucleation zone can preferably be between 100 Kelvin/seconds and 10000 Kelvin/seconds, particularly preferably between 2000 Kelvin/seconds and 3000 Kelvin/seconds and in the quench zone the cooling rate can preferably be between 1000 Kelvin/seconds and 50000 Kelvin/seconds, particularly preferably between 5000 Kelvin/seconds and 15000 Kelvin/seconds.

The residence time of the reaction mixture in the evaporation zone can preferably be between 0.1 seconds and 4 seconds, preferably between 0.5 seconds and 2 seconds, in the nucleation zone between 0.05 seconds and 1.00 seconds, preferably between 0.1 seconds and 0.2 seconds, in the oxidation zone between 5 milliseconds and 200 milliseconds, preferably between 10 milliseconds and 30 milliseconds, and in the quench zone between 0.05 seconds and 1.00 seconds, preferably between 0.1 seconds and 0.2 seconds.

The process can also be performed in such a way that air and/or oxygen and the fuel gas can be supplied to one or more points within the evaporation zone.

The zinc oxide powder can be separated from the gas stream by means of a filter, cyclone, washer or other suitable separators.

The powder according to the invention can be used as a sunscreen, as a vulcanising agent, a dye in inks, in synthetic resins, in pharmaceutical and cosmetic preparations, as a ceramic raw material, as a catalyst.

The novel zinc oxide powder according to the invention receives its properties, such as e.g. defined aggregate size and low transmission values in the UV range, which are important for applications in sunscreen formulations for example, through the novel production process. Unlike the prior art, which in the case of pyrogenic processes always starts from the oxidation of zinc vapour, in the process according to the invention the zinc vapour is cooled below the boiling point of zinc before oxidation. This leads to a nucleation, a formation of zinc crystallites. The mechanism of this formation and the structure of the crystallites is not explained. The morphology of the zinc powder can be varied by varying the process parameters, such as e.g. cooling rates, residence times and/or temperatures.

EXAMPLES

Analytical Methods

The BET surface area is determined according to DIN 66131.

The transmission electron micrographs were obtained with a Hitachi transmission electron microscope, model H-75000-2. Approximately 500 to 600 aggregates were analysed by means of the CCD camera in the transmission electron microscope.

The variable F(shape) equals the quotient of the minimum to the maximum aggregate diameter. The variable F(circle) is calculated as F(circle)=4n×average surface area)/2 (P), where P=circumference of the aggregates.

The variables F(shape) and F(circle) describe the deviation of a particle from a perfect circular shape. F(shape) and F(circle) are 1 for a perfect circular object. The lower the value, the further removed the object structure from the perfect circular shape.

The parameters are defined according to ASTM3849-89.

The surface properties are determined by large-area (1 cm$^2$) XPS analysis (XPS=X-ray photoelectron spectroscopy), both in the original condition and after 30 minutes, surface erosion by ionic bombardment (5 kev argon ions). Fine structures of the oxygen signals are determined by Gaussian/Lorentzian curve analyses for oxygen.

One-percent aqueous solutions are used for the transmission measurements. Dispersion is performed by means of an ultrasonic instrument from Bandelin Elektronik. The sonication period is one minute. The measurements are taken using a Perkin Elmer Lambda 2 UV/Vis Spectrometer.

The bulk density was determined in accordance with DIN-ISO 787/XI.

EXAMPLES

FIG. 1 shows a flow diagram of the process according to the invention with the process stages and the incoming and outgoing mass flows.

There is: I=evaporation; II=nucleation; III=oxidation; IV=quenching; A=zinc oxide powder+inert gas; B=zinc vapour, water, (fuel gas); C=Zinc particles, water, (inert gas, fuel gas); D=zinc oxide particles, water, (inert gas); a=fuel gas, air/O$_2$; b=cooling (inert gas); c=air/O$_2$; d=cooling gas.

Example 1

Zinc powder (250 g/h, particle size ≦5 μm) is conveyed by means of a nitrogen stream (1.5 m$^3$/h) into an evaporation zone, where a hydrogen/air flame (hydrogen: 4.25 m$^3$/h, air: 8.40 m$^3$/h, lambda=0.82) is burning. The zinc powder is evaporated here. The reaction mixture consisting of zinc vapour, hydrogen, nitrogen and water is then cooled to a temperature of 850° C. by the addition of 1 m$^3$/h nitrogen. 5 m$^3$/h oxidation air and 34 m$^3$/h quench air are then added, whereby the reaction temperature falls to values below 400° C. The zinc oxide powder obtained is separated from the gas stream by filtration.

Example 2

Same as Example 1, whereby the parameters are altered to the values shown in Table 1.

Example 3 (Comparative Example)

Same as Example 1, except with an excess of air compared to oxygen in the evaporation zone. The parameters are altered to the values shown in Table 1.

Example 4 (Comparative Example)

Same as Example 1, except with no nucleation zone, the temperature prior to oxidation does not fall below the boiling point of zinc. The parameters are altered to the values shown in Table 1.

The characterisation of the products obtained from these examples is shown in Table 2.

Evaluation of the image analysis reveals the clearest differences between the zinc oxide powders according to the invention and the prior art for the average surface area of the particles, the aggregate sizes and the shape factor F (circle).

XPS analyses were performed of the zinc oxide powders according to the invention from Examples 1 and 2. It was found that the moisture content as non-desorbable oxygen in the form of Zn—OH and Zn—$OH_2$ units is 55.5% (Example 1) and 48.3% (Example 2). The moisture is thus significantly higher for example in the Nanotek Zinc Oxide product from Nanophase Technologies.

Figure 2:
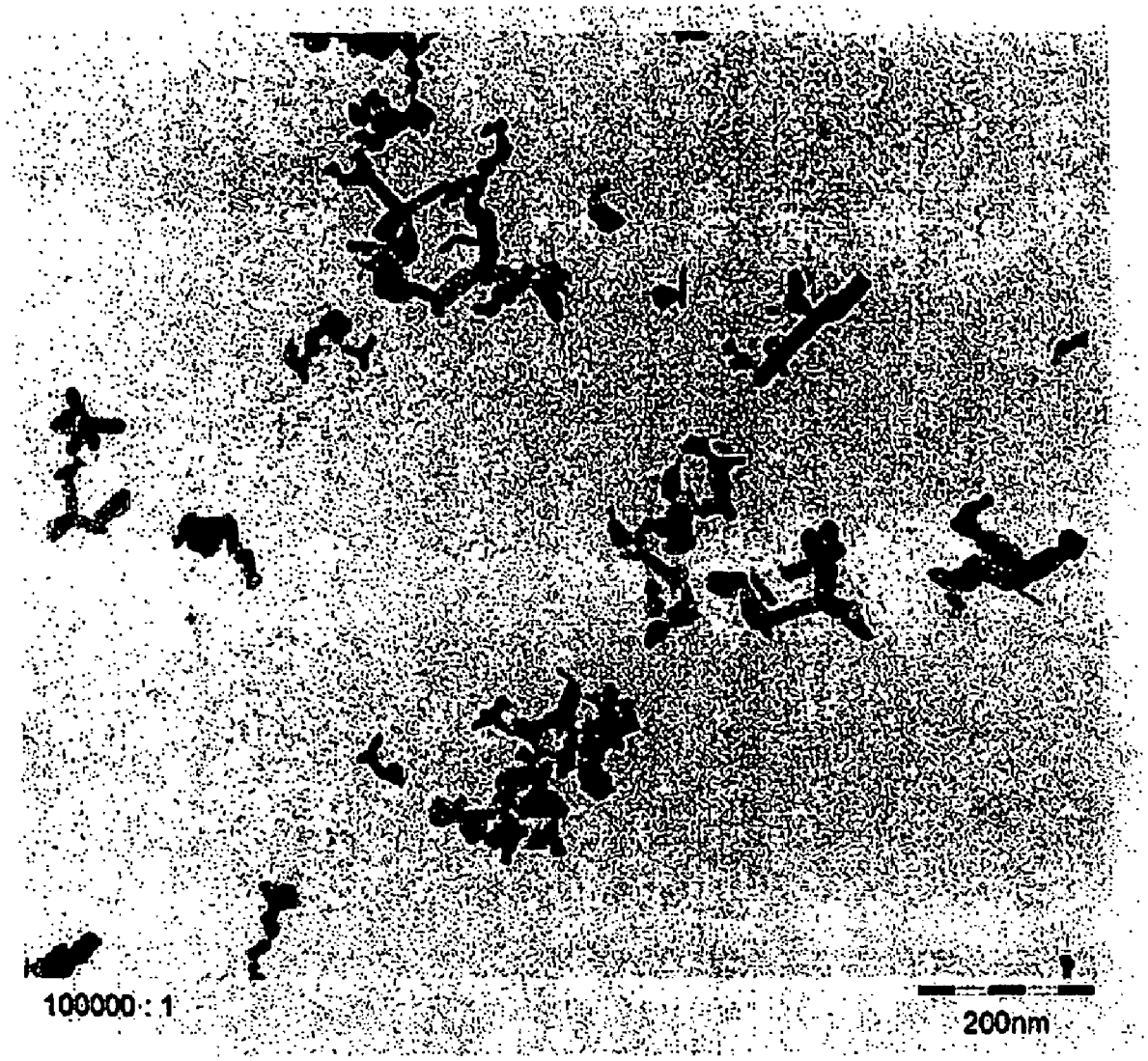
FIG. 2 shows a transmission electron micrograph of a powder according to the invention.

FIG. 2 shows a transmission electron micrograph of the powder according to the invention. Aggregates of nodular and acicular aggregates can clearly be seen.

TABLE 1

Process parameters

| | | | Example 1 | Example 2 | Example 3[1] | Example 4[1] |
|---|---|---|---|---|---|---|
| Evaporation | Zinc | g/h | 250 | 300 | 300 | 250 |
| | Nitrogen | $m^3/h$ | 1.5 | 1.5 | 1.0 | 2 |
| | Hydrogen | $m^3/h$ | 4.3 | 4.6 | 5 | 4.5 |
| | Air | $m^3/h$ | 8.4 | 9.0 | 22 | 20.5 |
| | Lambda | | 0.82 | 0.84 | 1.8 | 1.9 |
| Nucleation | Cooling gas | $m^3/h$ | 1 | 1.5 | 1 | 0.5 |
| | Temperature | °C. | 850 | 870 | 1050 | 960 |
| Oxidation | Oxidation air | $m^3/h$ | 5.0 | 4.0 | 4 | — |
| Quenching | Quench gas | $m^3/h$ | 34.0 | 30.0 | 10 | — |
| | Temperature | °C. | 285 | 296 | 424 | 526 |

[1]Comparative example

TABLE 2

Product properties

| | | Example 1 | Example 2 | Example 3[1] | Example 4[1] |
|---|---|---|---|---|---|
| BET surface area | $m^2/g$ | 36 | 20 | 7.5 | 16 |
| Average surface area | $nm^2$ | 5306 | 15762 | 61070 | 3220219 |
| Average aggregate diameter | nm | 75 | 133 | 186 | 515 |
| Average primary particle size | nm | 17 | 24 | 43 | 79 |
| Shape factor F(shape) | | 0.61 | 0.61 | 0.59 | 0.62 |
| Shape factor F(circle) | | 0.37 | 0.32 | 0.43 | 0.65 |
| Bulk density | g/l | 80 | 62 | 90 | 100 |
| Transmission | % | 50 | 56 | 60 | 66 |
| Morphology | | Predominantly nodular aggregates | Aggregates consisting of needles and nodules | Non-aggregated needles and tetrahedra | Predominantly needles, non-aggregated |

[1]Comparative example

The invention claimed is:

1. A process for the production of the composition comprising nanoscale pyrogenically produced zinc oxide powder wherein zinc powder is converted to zinc oxide powder in four successive reaction zones, wherein the four successive reaction zones are an evaporation zone, a nucleation zone, an oxidation zone and a quench zone, whereby in the evaporation zone the zinc powder conveyed there by an inert gas stream is evaporated in a flame of air and/or oxygen and a fuel gas, under the proviso that the reaction parameters are chosen such that oxidation of the zinc does not occur, to provide a hot reaction mixture consisting of zinc vapor, water vapor as a reaction product of forming the flame and, optionally, excess fuel gas, and whereby in the nucleation zone, the hot reaction mixture arrives from the evaporation zone, and cools to temperatures below the boiling point of zinc or is cooled to temperatures below the boiling point of zinc by means of an inert gas, thereby forming zinc crystallites, and whereby in the oxidation zone the mixture from the nucleation zone is oxidized with air and/or oxygen, and whereby in the quench zone the oxidation mixture is cooled to temperatures of below 400° C. by addition of cooling gas;

wherein the zinc oxide powder is separated from the gas stream.

2. A composition produced by the process of claim 1, comprising nanoscale pyrogenically produced zinc oxide powder having a BET surface area of 10 to 200 m²/g, wherein said composition is in the form of aggregates of anisotropic primary particles and that the aggregates display an average diameter of 50 to 300 nm, wherein the aggregates comprise a mixture of nodular primary particles and acicular primary particles, whereby the ratio of nodular to acicular primary particles is between 99:1 and 1:99.

3. A composition according to claim 2, wherein the nodular primary particles display an average diameter of 10 to 50 nm and the acicular primary particles a length of 100 nm to 2000 nm and a width of 10 nm to 100 nm.

4. A composition according to claim 2, wherein the aggregates display a largely anisotropic structure, defined by a shape factor F(circle) of below 0.5.

5. A composition according to claim 2, wherein the oxygen concentration at the surface of the powder as non-desorbable moisture in the form of Zn—OH and/or Zn—$OH_2$ units, determined by XPS analysis of the oxygen signals at 532 to 533 eV and 534 to 535 eV, is at least 40%.

6. A composition according to claim 2, wherein the transmission at a wavelength of 310 nm and 360 nm is no more than 60%.

7. A composition according to claim 2, wherein the bulk density is between 40 and 120 g/l.

8. Process according to claim 1, wherein in the evaporation zone, an excess of fuel gas is used, expressed in lambda values of 0.5 to 0.99.

9. Process according to claim 1, wherein the temperature in the evaporation zone is between 920° C. and 2000° C. and in the nucleation zone is between 500° C. and 900° C.

10. Process according to claim 1, wherein the cooling rate in the nucleation zone is between 100 Kelvin/seconds and 10000 Kelvin/seconds, and in the quench zone is between 1000 Kelvin/seconds and 50000 Kelvin/seconds.

11. Process according to claim 1 wherein the residence time in the evaporation zone is between 0.1 seconds and 4 seconds, in the nucleation zone is between 0.05 seconds and 1.00 seconds, in the oxidation zone is between 5 milliseconds and 200 milliseconds, and in the quench zone is between 0.05 seconds and 1.00 seconds.

12. A sunscreen comprising the composition as claimed in claim 2.

13. A vulcanizing agent comprising the composition as claimed in claim 2.

14. A dye or pigment comprising the composition as claimed in claim 2.

15. A ceramic raw material comprising the composition as claimed in claim 2.

16. A catalyst comprising the composition as claimed in claim 2.

17. Process according to claim 8, wherein the excess of fuel gas, expressed in lambda values is from 0.8 to 0.95.

18. Process according to claim 9, wherein the temperature in the nucleation zone is between 700° C. and 800° C.

19. Process according to claim 10, wherein the cooling rate in the nucleation zone is between 2000 Kelvin/seconds and 3000 Kelvin/seconds.

20. Process according to claim 10, wherein the cooling rate in the, quench zone is between 5000 Kelvin/seconds and 15000 Kelvin/seconds.

21. Process according to claim 11 wherein the residence time in the evaporation zone is between 0.5 seconds and 2 seconds.

22. Process according to claim 11 wherein the residence time in the nucleation zone is between 0.1 seconds and 0.2 seconds.

23. Process according to claim 11, wherein the residence time in the oxidation zone is between 10 milliseconds and 30 milliseconds.

24. Process according to claim 11, wherein the residence time in the quench zone is between 0.1 seconds and 0.2 seconds.

25. Process according to claim 1, wherein the zinc oxide powder is separated from the gas stream by means of a filter, cyclone, or washer.

* * * * *